United States Patent [19]

Urquhart et al.

[11] Patent Number: 4,851,231
[45] Date of Patent: * Jul. 25, 1989

[54] SYSTEM FOR DELIVERING DRUG IN SELECTED ENVIRONMENT OF USE

[75] Inventors: John Urquhart, Palo Alto; Felix Theeuwes, Los Altos, both of Calif.

[73] Assignee: ALZA Corporation, Palo Alto, Calif.

[*] Notice: The portion of the term of this patent subsequent to Feb. 24, 2001 has been disclaimed.

[21] Appl. No.: 26,427

[22] Filed: Mar. 16, 1987

Related U.S. Application Data

[60] Division of Ser. No. 651,408, Sep. 17, 1984, Pat. No. 4,721,631, which is a continuation of Ser. No. 448,956, Dec. 13, 1982, abandoned.

[51] Int. Cl.⁴ .......................... A61K 9/50; A61K 9/52; A61K 9/22; A61K 9/26
[52] U.S. Cl. ...................... 424/469; 424/468; 424/470; 424/484; 424/485; 424/486; 424/487
[58] Field of Search ............... 424/468, 469, 470, 484, 424/485, 486, 487

[56] References Cited

U.S. PATENT DOCUMENTS

| | | | |
|---|---|---|---|
| Re. 27,107 | 3/1971 | Levesque | 424/469 |
| 2,853,420 | 7/1956 | Lowey | 424/35 |
| 2,928,770 | 3/1960 | Bardani | 424/469 |
| 2,987,445 | 6/1961 | Levesque | 424/469 |
| 2,996,431 | 8/1961 | Barry | 424/469 |
| 3,087,860 | 4/1963 | Endicott | 424/469 |
| 3,867,519 | 2/1975 | Michaels | 424/19 |
| 3,903,297 | 9/1975 | Robert | 424/305 |
| 4,012,498 | 3/1977 | Kornblum | 424/19 |
| 4,096,238 | 6/1978 | Zaffaroni et al. | 424/15 |
| 4,135,514 | 1/1979 | Zaffaroni et al. | 424/20 |
| 4,177,256 | 12/1979 | Michaels et al. | 424/22 |
| 4,343,789 | 8/1982 | Kawata et al. | 424/35 |
| 4,434,153 | 2/1984 | Urquhart et al. | 424/22 |
| 4,522,625 | 6/1985 | Edgren | 424/32 |
| 4,578,075 | 3/1986 | Urquhart et al. | 604/892 |
| 4,642,233 | 2/1987 | Urquhart et al. | 424/486 |
| 4,649,043 | 3/1987 | Urquhart et al. | 424/486 |
| 4,659,558 | 4/1987 | Urquhart et al. | 424/486 |
| 4,721,613 | 1/1988 | Urquhart et al. | 424/488 |

OTHER PUBLICATIONS

Adler's *Physiology of the Eye*, p. 20, pub. 1975 by C. V. Mosby Co.
Bockus et al., *Gastroenterology*, pp. 300–304, pub. in 1963 by W. B. Saunders Co.
Malagelada et al., *Gastroenterology*, vol. 70, pp. 203–210, 1976, pub. by Williams & Williams Co.
Lachman et al., *The Theory and Practice of Industrial Pharmacy*, pp. 371, 374, and 375, pub. in 1976 by Lea & Febiger.

*Primary Examiner*—Shep K. Rose
*Attorney, Agent, or Firm*—Paul L. Sabatine; Edward L. Mandell; Steven F. Stone

[57] ABSTRACT

A delivery system is disclosed for delivering an agent to a selected environment of use having a pH of greater than 3.5.

1 Claim, 1 Drawing Sheet

SYSTEM FOR DELIVERING DRUG IN SELECTED ENVIRONMENT OF USE

CROSS REFERENCE TO RELATED APPLICATIONS

This application is a division of U.S. appln. Ser. No. 06/651,408 filed on Sept. 17, 1984, now U.S. Pat. No. 4,721,631 issued June 26, 1988 which application is a continuation of U.S. Pat. appln. Ser. No. 06/448,956 filed on Dec. 13, 1982, now abandoned.

FIELD OF THE INVENTION

This invention pertains to a novel system for delivering a beneficial drug in a selected environment of use. More particularly, the invention concerns a delivery system manufactured as a drug delivery device, and it comprises a multiplicity of tiny reservoirs containing a beneficial drug housed in a maxtrix formed of a pH sensitive material that releases the reservoirs in an environment having a pH of greater than 3.5.

BACKGROUND OF THE INVENTION

A critical and a pressing need exists presently for a delivery system that, (1) delivers a beneficial drug at a controlled rate and continuously in a biological environment having a pH of greater than 3.5 to 8.0 such as the intestine of an animal but, (2) does not deliver the drug in a biological environment having a pH of 1.0 to 3.5 inclusive, such as the stomach of an animal. The need arises because often it is contra-indicated and therapeutically undesirable to deliver many drugs in the stomach, and because often it is indicated and therapeutically desirable to deliver many drugs in the intestine. That is, some drugs do not lend themselves for delivery in the stomach, while some drugs lend themselves for delivery primarily in the intestine.

For example, drugs where administration in the stomach should preferably be avoided include, (a) drugs that are digested or decomposed in the acidic environment of the stomach such as the antibiotics erythromycin and carbenicillium; (b) drugs that induce nausea and vomiting such as emetine, atabrine and diethylstilbestrol; and, (c) drugs that act as stomach irritants such as chloride and iron salts, and anti-inflammatory drugs like aspirin, flufenamic acid, and phenylbutazone.

For example, drugs where administration in the intestine is preferred include, (d) intestinal antihelmitics such as bephenium hydroxynaphthoate, niclosammide, piperazine, thiabendazole and dichlorophen; (e) intestinal antibacterials such as methenamine, sulphasalazine and phthalylsulphthiazole; (f) antischistomals such as niridazoli; (g) antiprotozians such as dichlorophen; and, (h) drugs where it is desirable to dispense the medication in the intestine for initial absorption in the duodenum and jejunium, such as folic acid in the normal proximal jejunium.

The above presentations clearly teaches both the necessity and the urgency for a unique delivery system that substantially avoids delivering a drug in the stomach, but which delivery system can administer a drug in a therapeutically effective amount in the intestine over time. It will be appreciated by those versed in the drug dispensing art in view of this presentation, that if a delivery system is provided that can fulfill these demands, such a delivery system would have a positive value and represent also a substantial contribution to the dispensing art. Likewise, it will be appreciated by those skilled in the art, that if a delivery system is made available for releasing drug at a controlled rate over time in the intestine for achieving therapeutic levels, such a delivery system would be clinically useful in the practice of medicine.

OBJECTS OF THE INVENTION

Accordingly, in view of the above presentation it is an immediate object of this invention to provide a novel and useful drug delivery system that satisfies the necessity and the urgency for a delivery system that administers drug in the intestine for obtaining better therapy in the management of health and disease.

Another object of the present invention is to provide a drug delivery system having the combined effects of prompt initial drug delivery on entering into the intestine, and prolonged continuous administration of drug throughout the remainder of the intestine.

Another object of the invention is to provide a delivery system for administering a drug in the intestine, which system is relatively economical in cost to manufacture, provides the physician with a dependable drug delivery means, and is welladapted for practical and acceptable patient use.

Yet another object of this invention is to provide a delivery system embodying phusical-chemical properties that prevent release of drug in the stomach to reduce the risk of unwanted effects, and yet readily make available drug for absorption in the upper intestine and throughout the intestinal tract.

Another object of this invention is to provide a delivery system manufactured as a drug delivery device that is simple in construction and exhibits all of the practical benefits in controlled and continuous administration of drug during its prolonged residency in the intestine for executing a therapeutic program.

Still another object of the invention is to provide a delivery device comprising, (1) a matrix formed of a material that maintains its physical and chemical integrity in a first environment having a pH of 1.0 to 3.5 inclusive, and (2) a multiplicity of drug reservoirs in the matrix, which drug reservoirs are shielded by the matrix from the first environment, and released by the matrix as the devices pass into a second environment having a pH of greater than 3.5 to 8.0

These objects, as well as other objects, features and advantages of the invention, will become more apparent from the following detailed description of the invention, the drawings, and the accompanying claims.

BRIEF DESCRIPTION OF THE DRAWINGS

In the drawings, which are not drawn to scale, but are set forth to illustrate various embodiments of the invention, the Figures are as follows.

In the drawings and the specification, like parts in related Figures are identified by like numbers. The terms appearing earlier in the specification, and in the description of the drawings as well as embodiments thereof, are further described elsewhere in the disclosure.

DETAILED DESCRIPTION OF THE DRAWINGS

Turning now to the drawings in detail, which are in example of a manufacturing procedure and a delivery system provided by the invention, and which examples are not to be construed as limiting, one example of the manufacturing procedure and the delivery system are seen in FIGS. 1 through 5, considered together.

Figure 1:
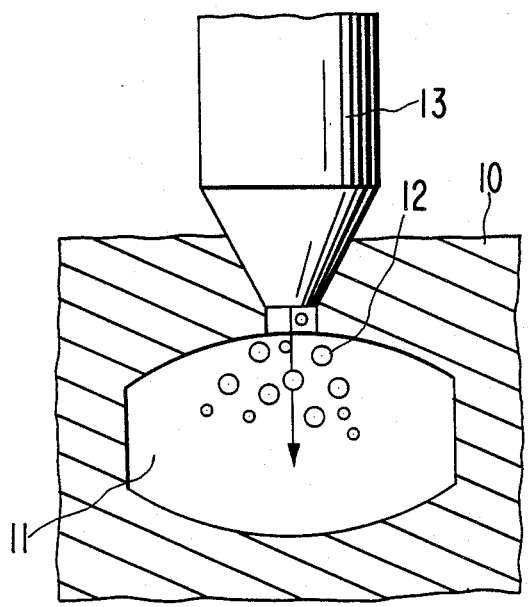
FIG. 1 is a view partly in section of a mold receiving a multiplicity of tiny reservoirs of drug from a filling hopper.

Turning first to FIG. 1, there is seen the first manufacturing step in the assembly line leading to the delivery system of this invention. FIG. 1 illustrates a mold 10 comprising a mold cavity 11 for receiving a multiplicity of tiny reservoir 12 from reservoir feeding hopper 13. Hopper 13 feeds a sufficient number of tiny reservoirs 12 into mold cavity 11 for filling said mold cavity 11.

Figure 2:
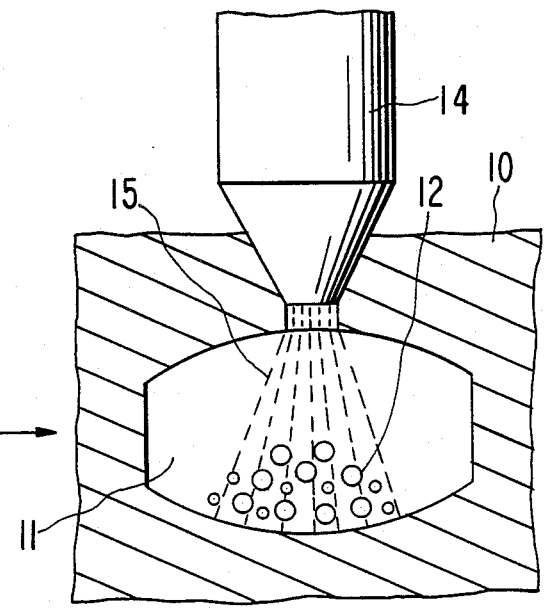
FIG. 2 is a view partly in opened section of a mold containing the tiny reservoirs of FIG. 1 and receiving a pH sensitive polymer.

FIG. 2 illustrates another step in the manufacture of the delivery system. In FIG. 2, mold 10 is positioned at the assembly line station for receiving from polymer feeding hopper 14, a pH sensitive polymer 15 in liquid form, that fills mold cavity 11 and forms a solid polymer matrix for tiny reservoirs 12.

Figure 3:
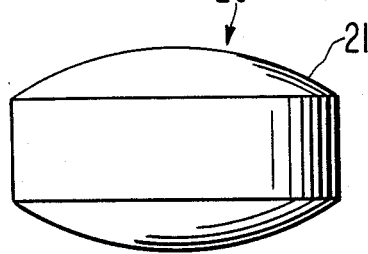
FIG. 3 is a view of the delivery system provided by the invention.
Figure 4:
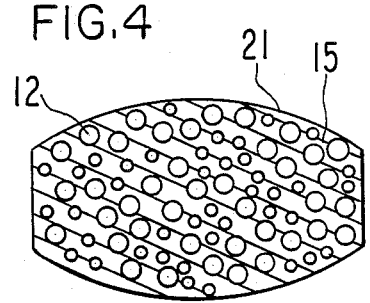
FIG. 4 is an opened-view in cross-section of the delivery system of FIG. 3 as manufactured by the processes of FIGS. 1 and 2.

FIG. 3 illustrates the delivery system 20 provided by the invention, and it comprises a matrix 21 that is adapted, shaped and sized for oral admittance into the gastrointestional tract of an animal, including a human. In FIG. 4, seen in opened section, matrix 21 comprises a solid, non-toxic polymer 15, represented by solid lines, which matrix 21 houses a multiplicity of tiny reservoirs 12 for the controlled delivery of a beneficial agent over time. The polymer material 15 forming matrix 21 is pH sensitive. That is, it is inert, or maintains its physical and chemical integrity at a pH up to and including 3,5, and at a pH of greater than 3.5 it looses its physical and chemical integrity and releases tiny reservoirs 12 for them to act both independently and collectively for delivering beneficial agent to the environment of use.

Figure 5:
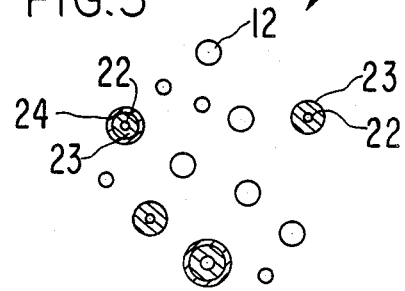
FIG. 5 depicts a multiplicity of tiny reservoirs, some in opened cross-section on their release from the delivery system of FIG. 4.

In FIG. 5, individual tiny reservoirs 12 are seen in detail, some in cross-section, and they comprise a core of beneficial agent 22 surrounded by a wall 23 formed of a release rate controlling material. Tiny reservoirs 12 can have wall 23 formed of a single layer, or of more than one layer 24 comprising like or unlike release rate controlling materials. The layers comprising 23 and 24 can be of the same or different thickness. Additionally, the materials forming wall 23, 24, can be selected from materials that release agent 22 by different physical-chemical mechanisms. These mechanism include diffusion, osmosis, erosions, and metabolism in an environment having a pH of greater than 3.5. Various thicknesses of wall forming materials can be used as an aid for providng additional controlled release of beneficial agent.

In operation, delivery system 20 operates by maintaining its integrity in an environment having a pH of from 1.0 to 3.5 inclusive, such as the stomach, and essentially does not release tiny reservoirs 12 in this environment. On passing into an environment having a pH of greater than 3.5 to 8.0, such as the intestine, system 20 undergoes change by dissolving, dissolution, or the like, and releases tiny reservoirs 12 into the intestine. In the intestine, tiny reservoirs 12 deliver agent 22 over a prolonged period of time.

DETAILED DESCRIPTION OF THE INVENTION

In accordance with the practice of this invention, delivery system 20 comprising matrix 21 is formed of a polymer 15 that keeps its physical and chemical integrity in a biological environment having a pH of from 1.0 to 3.5 inclusive. Polymer 15 forming pH-sensitive matrix 21 of nontoxic, is physiologically inactive, and it does not adversely effect drug 22 and a host. Polymer 15 dissolves, disintegrates, degrades, hydrolyzes, solubilizes, is digested, or it undergoes like change in a biological environment at a pH greater than 3.5 to 8.0, thereby pH-releasing tiny timed reservoirs 12 into the bioligical environment. The product of polymer 15 produced on releasing reservoirs 12 is nontoxic, chemically inert, and physiologically inactive. In operation, matrix 21 keeps it integrity and provides structural support for reservoirs 12 during the period of time delivery system 20 is in the stomach and travels therethrough. Then, as delivery system 20 passes into the intestine, matrix 21 releases reservoirs 12 for reservoirs 12 to delivery drug over the prolonged period of time reservoirs 12 travels through the intestine.

Examples of matrix forming materials suitable for the present purpose include, (a) polymers having at least one acidic group that enables it to keep its integrity in a low pH environment, but releases the reservoirs in a higher pH environment, (b) polymers that undergo change in a higher pH environment by enzymes present in that environment, (c) polymer compositions comprising a polymer and another agent that promote at a higher pH the disintegration of the matrix, such as a polymer and a fat, fatty acid, wax and the like, and correspondingly the release of the reservoir, and (d) polymeric compositions comprising a polymer and agent such as a bile, cholesterol, or the like, that form complexes that disintegrate in a higher pH environment and concomitantly release the tiny timed reservoirs containing drug.

Representative of polymers that keep their integrity at a pH of 1.0 to 3.5 inclusive are polyacidic polymers having acid groups in an undissociated form in this pH range, such as vinyl derivatives of partially hydrolyzed styrenemaleic anhydride copolymer, methylmethacrylate-methacrylic acid copolymer, polymethacrylic acid ester, methylacrylatemethacrylic acid ester, partial alkylene glcol ether esters of $C_1$ to $C_4$ alkyl acrylate unsaturated carboxylic acid anhydride copolymers including maleic, citraconic or itaconic carboxylic acid anhydride, and the like.

Representative of additional polymers that keep their integrity at a pH of 1.0 to 3.5 inclusive, are cellulose carboxylic acid esters, cellulose carboxylic acid ethers, such as cellulose ethyl phthalate, cellulose acetate phthalate, starch acetate phthalate, amylose acetate phthalate, hydroxypropyl methylcellulose phthalate, alkali salts of cellulose acetate phythalate such as sodium salt cellulose acetate phthalate, alkaline earth salts of acidic cellulose esters such as calcium salt of cellulose acetate phthalate, ammonium salts of acidic cellulose esters such as ammonium salt of hydroxypropyl methylcellulose phthalate, cellulose acetate hexahydrophthalate, hydroxypropyl methylcellulose hexahydrophthalate, and the like.

Representative of other polymers and polymer compositions comprising at least two ingredients operable for the present purpose of keeping their integrity in a pH range of 1.0 to 3.5 inclusive, are polymers such as shellac, ammoniated shellac, formalized gelatin, polyvinyl acetate phthalate, polyvinyl acetate hydrogenphthalate, and the like; and polymer compositions such as a mixture of hydroxypropyl methylcellulose phthalate and triacetate glycerol in a weight to weight ratio of 99 to 1, shellac-formalized gellatin composition, styrene-maleic acid copolymer dibutyl phthalate composition, styrene-maleic acid polyvinyl acetate phthalate, shellac stearic acid, and the like. The maxtrix forming polymer compositions can contain small amounts, about 0.01 to 3 weight percent, or slightly more of a plasticizer such as esters of saturated and unsaturated fatty acids, of hydroxy carboxylic acids with ols such as alcohols and clycols, mono and draikyl phalates, and the like. Also, the polymeric composition can include a small amount, about 0.01 to 3 weight percent, or slightly more, of a filler such as carbon, talc, waxes, and the like. The matrix forming polymeric compositions can include also a binder such as sucrose, gelatin, gums, polyvinyl-pyrrolidone, polyethylene glycol, and the like.

Matrix 21 comprising polymer 15 and tiny timed release reservoirs 12 can be made by conventional manufacturing methods. These methods include solution forming and compression forming processes. In the solution forming process, polymer 15 is mixed with a solvent and poured into mold cavity 11 containing reservoirs 12. Then, the solvent is stripped from mold cavity 11 by heat, vacuum, air blowing, or the like, causing polymer 15 to solidify yielding matrix 21 with reservoirs 12 releasably contained therein. Solvents operable for this purpose include methanol, ethanol, acetone, methanol-ethylcelloslove, alcohol-acetone, methylene-chloride, methylene chloride-ethanol, methylene chloride-acetone; and the like. Examples of polymer 15 and a solvent combination are polyvinyl acetatephthalate and acetone, methylacrylate-methacrylic acid copolymer and acetone, polyacrylic acid ester and acetone, hydroxypropyl methylcellulose phthalate and acetone, hydroxypropyl methylcellulose phthalate and methanol-acetone, hydroxypropyl methylcellulose phthalate and ethanol-acetate, cellulose acetate phthalate and acetone, cellulose acetate phthalate and methanol, 2-methyl-5-vinylpyridine methacrylate-methacrylic acid copolymer and ethanol, and the like.

The compression forming process is carried out by charging mold cavity 11 containing reservoirs 12 with polymer 15, or polymer composition 15 in powdered, particle, or like form, and then mold cavity 11 ingredients are compressed compartively hard to form matrix 21 containing reservoirs 12. The term hard as used for the present purpose denotes a delivery system htat keeps its physical and chemical integrity in the low pH range, thereby delaying release of the reservoirs and in vivo availability of the medicament until the delivery system passes into the higher pH biological environment. Matrix 21 can be formed by conventional compression machines such as Noyes, Stokes, Manesty machines, and the like. The pressure force applied to form the matrix-reservoir delivery system has a hardness of at least 4 kilograms, kg. More preferably, the force is from 6 to 20 kg, and in a presently preferred embodiment, a force of 15 to 20 kg is applied over the surface of the ingredients in mold cavity 11. The force used is sufficient to minimize possible premature swelling of delivery system 20 in the low pH environment and it substantially prevents the passage of a low pH fluid into the delivery system. it is also presently preferred embodiment, that reservoirs 12 be disposed in mold cavity 11 such that polymer 15 forms an exterior perimeter to lessen reservoirs 12 contact with the exterior of matrix 12 for essentially eliminating premature release of reservoirs 12 and delivery of medicament 22. Generally, delivery system 20 can have any operable shape corresponding to the shape of the die, such as square, rectangle, round, oblong and the like. The compression process used by the invention provides advantages, such as a solvent is not needed to compress the matrix, it provides a system having a uniform release of reservoirs in the higher pH environment, tacky powdered polymer can be used as an aid in compressing the matrix, and the like.

Tiny reservoirs 12 used for the purpose of this invention provide for the controlled delivery of drug 22 over a prolonged period of time. Tiny reservoirs 12 comprise a drug 22 surrounded by a wall 23 of a drug release rate controlling material that delivers drug 22 in the biological environment having a pH of greater than 3.5 to 8.0. The prolonged period of time for the purpose of this invention corresponds to the period of time reservoirs 12 are in this environment. The materials forming wall 23 are in a presently preferred proviso different materials than the materials forming matrix 21, and they can be selected from materials that release drug 22 by different physical-chemical mechanisms in a bioligical environment having a pH of greater than 3.5 to 8.0. These mechanisms include erosion, diffusion, osmosis, metabolism, and the like. Wall 23 can have various thicknesses and layers as an additional aid for providing timed release of drug 22.

Wall 23 of tiny reservoirs 12 surrounding drug 22 can be a wall-forming composition consisting essentially of a fatty ester mixed with a wax, such as a triglyceryl ester selected from the group consisting of glyceryl distearate, glyceryl tristearate, glyceryl monostearate, glyceryl dipalmitate, glyceryl tripalmitate, glyceryl monolaurate, glyceryl didocosanoate, glyceryl tridocosanoate, glyceryl monodocosanoate, glyceryl monocaprate, glyceryl dicaprate, glyceryl tricaprate, glyceryl monomyristate, glyceryl dimyristate, glyceryl trimyristate, glycerol monodicenoate, glyceceryl didecenoate and glyceryl tridecenoate.

The wax included in the wall forming composition is a member selected from the group consisting essentially of beeswax, cetyl palmitate, spermacetic wax, carnauba wax, cetyl myristate, cetyl palitate, cetyl cerolate, stearyl palmitale, stearyl myristable, and lauryl laurate.

The wall forming composition comprising the ester and the wax can be coated around the drug by using an organic solvent such as a member selected from the group consisting of carbon tetrachloride, chloroform, trichloroethylene, ether, benzene, ethyl acetate, methyl ethyl ketone, isopropyl alcohol, and the like. The fatty esters, waxes, solvents and procedures for making tiny reservoirs that slowly disintegrate and continuously provide drug over a period of 10 to 12 hours are disclosed in U.S. Pat. No. 2,793,979.

Wall 23 of tiny reservoir 12 in another embodiment is formed of an osmotic wall forming material that releases drug 22 at a controlled rate by the process of osmotic bursting over time. Drug 22 in this embodiment is present in the form of an osmotic solute, such as therapeutically acceptable salt, and it exhibits as osmotic pressure gradient across wall 23 against an external fluid. The membrane material used to form wall 23 is permeable to the passage of an external fluid and substantially impermeable to the passage of drug 22. Typical material includes a member selected from the group consisting of cellulose ester, cellulose ether, cellulose acylate, diacylate, cellulose triacylate, cellulose acetate, cellulose diacetate, cellulose triacetate, cellulose acetate having a degree of substitution, D.S. up to 1 and an acetyl content of 21%, cellulose diacetate having a D.S. of 1 to 2 and an acetyl content of 21 to 35%, cellulose triacetate having a D.S. of 2 to 3 and an acetyl content of 35 to 44.8%, cellulose acetyl propionate, cellulose acetate butyrate, and the like. The osmotic wall can be coated around the drug in varying thicknesses by pan coating, spray-pan coating, Wurster fluid air suspension coating and the like. Wall 23 is formed using organic solvents, including these mentioned above, and solvent systems such as methylene chloride-methanol, methylene chloride-acetone, methanol-acetone, ethylene dichloride-acetone, and the like. Osmotic wall forming procedures are disclosed in U.S. Pat. Nos. 2,799,241; 3,952,741; 4,014,334; and 4,016,880.

Wall 23 in another embodiment can be made of a drug release rate controlling material that releases drug by the process of diffusion. That is, drug 22 dissolves in wall 23 and passes through wall 23 at a controlled rate over time to the biological environment having a pH of greater than 3.5 to 8.0. Exemplary materials useful for forming a diffusional wall inclue ethylene-vinyl acetate copolymer, ethyl cellulose, polyethylene, cross-linked polyvinyl pyrrolidone, vinylidene chloride acrylonitrile copolymer, polypropylene, silicone, and the like. The wall can be applied by the techniques described above, and materials suitable for forming wall 23 are described in U.S. Pat. Nos. 3,938,515; 3,948,262; and 4,014,335.

Wall 23 in another embodiment can be made of a bioerodible material that bioerodes at a controlled rate and release drug 22 to a biological environment of use having a pH of greater than 3.5 to 8.0. Bioerodible materials useful for forming wall 15 include polyvalent alkali mobile cross-linked polyelectrolytes, polycarboxylic acid, polyesters, polyamides, polyimides, polylactinc acid, polyglycolic acid, polyorthoesters, and polycarbonate polymers that erode in the pH of greater than 3.5 to 8.0. The polymers and the procedures for forming wall 23 are disclosed in U.S. Pat. Nos. 3,811,444; 3,867,519; 3,888,975; 3,971,367; 3,993,057; and 4,138,344.

In the specification and the accompanying claims the term drug denotes pharmacologically beneficial substances that are absorbed in an intestinal environment by one or more of the following transport mechanisms: active transport, passive transport, pore transport, or facilitated transport to produce a local or systemic effect in animals. The term animals as used herein includes warm-blooded mammals such as humans. The benefical drug that can be delivered in a biological environment having a pH greater than 3.5 to 8.0 are drugs that act on the central nervous system, depressants, hypnotics, sedatives, phychic energizers, tranquilizers, muscle relaxants, antiparkinson, analgesics, anti-inflammatory, hormonal, contraceptives, sympathomimetics, diuretics, antiparasites, neoplastics, hypoglycemics, electrolytes, cardiovascular, anthelmintics, and the like.

Exemplary drugs that are administered in an environment having a pH greater than 3.0 to 8 include hycanthone, aminophyline, aminosalicylic acid, chymotrypsin, sulfoxone sodium, diethylstilbestrol, erythromycin estolate, erythromycin, orenzyme, carbomycin, riboflavin, thiamine, vitamin $D_2$, vitamin $D_3$, vitamin $B_{12}$, nitrogen mustard derivatives, phenylbutazone, acetysalicylic acid, helmintheasis xanthones, helminthiasis thioxanthones, narcotics morphine and codeine, deriviatives of phyrimedines including 5-fluorouracil and 5-brommouracil, quaternary ammonium compounds including benzomethamine, oxyphenonium, hexamethonium, and tubocurarine, atropine, and the like. The beneificial drugs are known in the art in *Pharmaceutical Sciences,* by Remington, 1980, published by Mack Publishing Co.; *Physicians' Desk Reference,* 36 Edition, 1982, published by Medical Economics Co.; and, *Medicinal Chemistry,* 3rd Edition, Vol. 1 and 2, by Burger, published by Wiley-Interscience Co.

Drug 22 can be present in tiny reservoirs 12 in various forms, such as uncharged molecules, molecular complexes, as therapeutically acceptable addition salts such as hydrochloride, hydrobromides, sulfates, oleates, and the like. For acid drugs, salts of metals, amines, organic cations, quaternary ammonium salts can be used. Derivatives of drugs such as esters, ethers and amides can be used. A drug that is water insoluble can be used in a form that is a water soluble derivative thereof to serve as a solute, and on its release from the delivery system is converted by enzymes, hydrolyzed by body pH, or other metabolic processes to the original biologically active form.

The amount of drug present in a tiny timed reservoir generally is about 10 ng to 25 mg. For some drug, a slightly higher amount may be present in the reservoir. The number of tiny timed reservoirs present in a delivery system is about 10 to 1000, and preferably for an oral delivery system about 100 to 150. The tiny reservoirs comprising the wall and the inner drug core have a diameter of about 100 microns, and in a presently preferred embodiment a diameter of about 2000 microns. For oral use, the delivery system comprising the matrix and the tiny reservoirs homogenously or heterogenously housed therein, can have conventional shapes such as round, oval and the like. The delivery system can have a diameter of 4 mm to 15 mm, and the like.

The following examples will serve to further illustrate the invention. A delivery system manufactured and sized, shaped and adapted as an orally administrable tablet containing tiny reservoirs of a sympathomimetic drug is prepared as follows: first, powdered drug is mixed with sucrose and the blend passed through a 15 to 30 mesh screen to yield a multiplicity of cores of drug. Then, a drug release rate wall forming composition comprising 85% glycerol monostearate and 15% beeswax in warm carbon tetrachloride is spayed over the cores in a revolving coating pan until a wall is formed that surrounds individually and separately each drug core. Next, the coating solvent is stripped from the tiny reservoirs, and a series of mold cavities are charged with 50 tiny reservoirs and 200 mg of a matrix forming pH sensitive powdered polymer. The matrix forming polymer, slightly tacky cellulose acetate phthalate, is a different polymer than the polymer composition used to form the wall of the reservoirs. Finally, the filled mold cavity is pressed under a pressure of 18 kg to yield the delivery system.

Another drug delivery system is provided by coating a drug core, for example, procainamide hydrochloride, in a fluid air suspension with a wall forming composition of ethyl cellulose in ethanol to surround the drug core with ethyl cellulose, to yield the tiny reservoirs. After the solvent is vacuum stripped from the tiny reservoirs, the reservoirs are blended with ground tacky shellac and pressed into an oral tablet.

The above manufacture can be repeated by replacing the ethyl cellulose and ethanol with cellulose acetate having an acetyl content of 32% and methylene chloride-methanol solvent and then dispersing the tiny reservoirs in a pH releasable matrix comprising sticky polyvinylacetate phthylate; or, by applying a dioerodible wall of poly(2,2-dioxo-trans-1,4-cyclohexane dimethylene tetrahydrofuran) around the drug core. The latter polymer is applied by heating the polymer to 80°–90° C., and then dispersing a multiplicity of tiny reservoirs in matrix forming polyvinylacetate phthalate.

In another example, a delivery system is made by first preparing sustained intestinal release tiny reservoirs by blending 400 ml of ethyl cellulose-water, 70:30% solution, with 375 g of aminophylline, 150 g of mannitol and 475 g of magnesium stearate, and the blend kneaded and passed through an extrusion granulation machine. After drying a 115°–120° F., the reservoir forming drug cores are passed through a 20 mesh screen and then coated with a wall of ethyl cellulose in an air suspension machine to yield the tiny reservoirs. The number of coats surrounding the drug core is variable, usually 1 to 10 separate coats are used for the present purpose. Next, a multiplicity of reservoirs are blended with very slightly aqueous moist granulated sodium hydroxypropyl methylcellulose phthalate and the blend fed into the mold cavity of a tablet compressing machine. Then, the blend is compressed under a pressure head of at least 16 kg/cm$^2$ and under vacuum to yield the delivery system.

Other drug delivery systems are made by spraying nonpareil cores with an erodible, non-toxic adhesive and then dusting with drug. The drug-coated core is coated with an appropriate number of non-toxic intestinal drug release rate polymer composition to yield the tiny reservoirs. The number of polymer composition coating is variable, usually at least 1 to 20 separate coats. Finally, the tiny reservoirs are housed in a pH sensitive reservoir. The tiny reservoirs also can be made from a core of carbohydrate, such as sucrose, dusted with a mixture of talc, starch and galactose, moistened with distilled or deconized water, then dusted with the desired medicinal, such as the antibiotic erythromycin, and then coated with a reservoir wall forming polymer composition. The reservoirs are dried and then suspended in a solid matrix selected from the group consisting of a polymer composition of at least two wall forming members such as shellac and ammoniated shellac, polyvinyllactate phthalate, a blend of polyvinyllactate phthalate and polyvinyllactate phthalate, and the like.

It will be appreciated by those versed in the delivery art the present invention advances the state-of-the-art by providing (a) a delivery system comprising tiny reservoirs that release drug is an environment having a pH greater than 3,5, which tiny reservoirs do not require an additional cost that prevents their releasing drug in an environment having a pH up to 3.5 inclusive, as they are individually housed in an environment protective matrix; (b) by providing a delivery system that substantially protects the drug from the digestive processes of the stomach; (c) by providing a delivery system that substantially elimiminates irritating the mucous membranes of the stomach by shielding the drug from contact with the membranes; (d) by providing a delivery system that delivers drugs to the intestinal tract in their therapeutically active forms at a controlled and constant rate of delivery throughout the intestinal tract during the period of time the tiny reservoir traverse the intestine, and correspondingly establishing in an animal recipient drug blood drug levels exhibiting a decrease in peak and valleys of drug which may lead to ing a decrease in peak and valleys of drug which may lead to unwanted results; and (e) by providing a delivery system that embodies delayed onset of delivery at a later time with the capability of dispersing drug delivered over the intestinal tract to enhance drug absorption and/or local treatment of the color. Also, it will be understood by those knowledgeable in the delivery art that many embodiments of this invention can be made without departing from the spirit and scope of the invention, and the invention is not to be construed as limiting; as it embraces all equivalents thereof.

We claim:

1. An oral delivery system for delivering a beneficial drug, the delivery system comprising:
    (a) a body comprising a matrix sized and shaped and adapted for oral admittance into the gastrointestinal tract, the matrix comprising a pharmaceutically acceptable polymeric composition that substantially maintains its physical and chemical integrity in the stomach of the gastrointestinal tract, the composition being a member selected from the group consisting of shellac, ammoniated shellac, formalized gelatin, polyvinyl acetate phthalate, polyvinyl acetate hydrogenphthalate, styrene-maleic acid copolymer dibutyl phthalate, and styrene-maleic acid polyvinyl acetate phthalate;
    (b) a multiplicity of reservoirs in the body, the reservoirs comprising a diameter of about 100 to 2000 microns, said reservoirs comprising:
        (1) a beneifical drug;
        (2) a wall surrounding the beneifical drug, which wall comprises a drug-releasing bio-eroding, diffusion, dissolution or osmotic innocuous composition, said composition comprising a member selected from the group consisting of a fatty acid ester and a wax, a cellulose ester, a cellulose ester, an ethylene-vinyl acetate copolymer, ethyl cellulose, a polyester, polylactic, polygloycolic and polyester, that releases the beneficial drug in the intestine of the gastrointestinal tract; and,
    (c) wherein, when the delivery system is in operation in the stomach, the delivery system maintains its physical and chemical integrity, and when the delivery system enters the intestine, the delivery system releases the multiplicity of reservoirs in response to the intestine in which intestine the reservoirs deliver the beneficial drug over time.

* * * * *